(12) United States Patent
Lewicke et al.

(10) Patent No.: US 7,530,956 B2
(45) Date of Patent: May 12, 2009

(54) DAYTIME/NIGHTTIME RESPIRATION RATE MONITORING

(75) Inventors: Aaron Lewicke, Forest Lake, MN (US); Yi Zhang, Blaine, MN (US); John D. Hatlestad, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 88 days.

(21) Appl. No.: 11/820,002

(22) Filed: Jun. 15, 2007

(65) Prior Publication Data

US 2008/0312541 A1  Dec. 18, 2008

(51) Int. Cl.
*A61B 5/00* (2006.01)

(52) U.S. Cl. .................. 600/538; 600/529; 600/483

(58) Field of Classification Search .............. 600/484, 600/529
See application file for complete search history.

(56) References Cited

U.S. PATENT DOCUMENTS

| | | | |
|---|---|---|---|
| 6,128,534 A | 10/2000 | Park et al. | |
| 6,440,066 B1 * | 8/2002 | Bardy | ............ 600/300 |
| 6,454,719 B1 * | 9/2002 | Greenhut | ............ 600/484 |
| 6,589,188 B1 | 7/2003 | Street et al. | |
| 6,599,250 B2 | 7/2003 | Webb et al. | |
| 6,600,949 B1 | 7/2003 | Turcott | |
| 6,714,811 B1 | 3/2004 | Padmanabhan et al. | |
| 6,731,984 B2 | 5/2004 | Cho et al. | |
| 6,741,885 B1 | 5/2004 | Park et al. | |
| 6,752,765 B1 | 6/2004 | Jensen et al. | |
| 6,773,404 B2 | 8/2004 | Poezevera et al. | |
| 7,094,207 B1 | 8/2006 | Koh | |
| 2004/0111040 A1 | 6/2004 | Ni et al. | |
| 2005/0042589 A1 | 2/2005 | Hatlestad et al. | |
| 2005/0080348 A1 * | 4/2005 | Stahmann et al. | ........... 600/529 |
| 2006/0241513 A1 | 10/2006 | Hatlestad et al. | |

(Continued)

FOREIGN PATENT DOCUMENTS

WO    WO-98/33553    8/1998

(Continued)

OTHER PUBLICATIONS

Charach, Gideon, et al., "Transthoracic monitoring of the impedance of the right lung in patients with cardiogenic pulmonary edema", *Critical Care Medicine*, 29(6), (Jun. 2001), 1137-44.

(Continued)

*Primary Examiner*—Robert L Nasser
(74) *Attorney, Agent, or Firm*—Schwegman, Lundberg & Woessner, P.A.

(57) ABSTRACT

A device and method can monitor or trend a patient's respiration rate measurements according to the time of day. The device, which may be implantable or external, collects and classifies respiration rate measurements over time. The trended information about particular classes of respiration rate measurements is then communicated to a remote external device, which in turn provides an indication of heart failure decompensation. Examples of classes of respiration rate measurements include a daily maximum respiration rate value, a daily minimum respiration rate value, a daily maximum respiration rate variability value, a daily minimum respiration rate variability value, and a daily central respiration rate value. These respiration rate measurements can be further classified into daytime or nighttime respiration rate measurements.

17 Claims, 7 Drawing Sheets
(1 of 7 Drawing Sheet(s) Filed in Color)

U.S. PATENT DOCUMENTS

2007/0129643 A1* 6/2007 Kwok et al. .............. 600/529
2007/0135725 A1* 6/2007 Hatlestad .................. 600/529

FOREIGN PATENT DOCUMENTS

| WO | WO-99/58056 | 11/1999 |
| WO | WO-00/51492 | 9/2000 |
| WO | WO-01/70103 A2 | 9/2001 |
| WO | WO-02/40096 A1 | 5/2002 |

OTHER PUBLICATIONS

Ekman, I., et al., "Symptoms in patients with heart failure are prognostic predictors: insights from COMET", *J Card Fail.*, 11(4), (May 2005),288-92.

Hatlestad, John, "Systems and Methods for Determing Respiration Metrics", U.S. Appl. No. 11/300,675, filed Dec. 14, 2005, CPI No. 05-382, 51 pgs.

Lee, D. S., et al., "Predicting mortality among patients hospitalized for heart failure: derivation and validation of a clinical model", *JAMA*, 290(19), (Nov. 19, 2003),2581-7.

Rame, J. E., et al., "Outcomes after emergency department discharge with a primary diagnosis of heart failure.", *Am Heart J.*, 142(4), (Oct. 2001),714-9.

Schiff, G. D., et al., "Decompensated heart failure: symptoms, patterns of onset, and contributing factors.", *Am J Med.*, 114(8), (Jun. 1, 2003),625-30.

Spengler, C. M., et al., "An endogenous circadian rhythm of respiratory control in humans", *J Physiol.*, 526 Pt 3, (Aug. 1, 2000),683-94.

Stephenson, R., et al., "Circadian rhythms in the chemoreflex control of breathing.", *Am J Physiol Regul Integr Comp Physiol.*, 278(1), (Jan. 2000),R282-6.

Zhang, Yi, et al., "Rapid Shallow Breathing Detection for Use in Congestive Heart Failure Status Determination", U.S. Appl. No. 11/229,316, filed Sep. 16, 2006, 55 pgs.

* cited by examiner

DAYTIME/NIGHTTIME RESPIRATION RATE MONITORING

TECHNICAL FIELD

This document pertains generally to respiration detection and monitoring, and more particularly, but not by way of limitation, to daytime/nighttime respiration rate monitoring.

BACKGROUND

Monitoring respiration rate measurements in cardiac patients is important for predicting, detecting, and managing acute decompensated heart failure (HF). For example, a decompensating CHF patient may experience respiratory symptoms such as dyspnea or low rapid shallow breathing.

OVERVIEW

This document describes, among other things, a device and method can monitor or trend a patient's respiration rate measurements according to the time of day. The device, which may be implantable or external, collects and classifies respiration rate measurements over time. The trended information about particular classes of respiration rate measurements is then communicated to a remote external device, which in turn provides an indication of heart failure decompensation. Examples of classes of respiration rate measurements include a daily maximum respiration rate value, a daily minimum respiration rate value, a daily maximum respiration rate variability value, a daily minimum respiration rate variability value, and a daily central respiration rate value. These respiration rate measurements can be further classified into daytime or nighttime respiration rate measurements.

Example 1 describes a method. In this example, the method comprises detecting a respiration signal from a subject; determining respiration rate or interval measurements from the respiration signal; classifying the respiration rate or interval measurements into at least one class of respiration rate or interval measurements, the class corresponding to a specified time of day; trending information about a particular class of respiration rate or interval measurements; and providing a heart failure decompensation indication using the trended information.

In Example 2, the method of Example 1 optionally comprises determining respiration rate or interval measurements from the respiration signal by excluding one or more periods of apneic breathing.

In Example 3, the method of one or any combination of Examples 1-2 optionally comprises classifying the respiration rate or interval measurements into at least one of the following classes: a daily maximum respiration rate value, a daily minimum respiration rate value, a daily maximum respiration rate variability value, a daily minimum respiration rate variability value, and a daily central respiration rate value.

In Example 4, the method of one or any combination of Examples 1-3 optionally comprises classifying the respiration rate or interval measurements into a specified one of daytime respiration rate or interval measurements or nighttime respiration rate or interval measurements.

In Example 5, the method of one or any combination of Examples 1-4 optionally comprises collecting the specified one of the daytime or nighttime respiration rate or interval measurements; performing a statistical analysis on the collected respiration rate or interval measurements; and providing the heart failure decompensation indication using a result of the statistical analysis.

In Example 6, the method of one or any combination of Examples 1-5 optionally comprises providing the heart failure decompensation indication by detecting a change over time in a measure of centrality of the collected respiration rate or interval measurements.

In Example 7, the method of one or any combination of Examples 1-6 optionally comprises providing the heart failure decompensation indication by detecting a change over time in a measure of spread or variance of the collected respiration rate or interval measurements.

In Example 8, the method of one or any combination of Examples 1-7 optionally comprises trending information about a particular class of respiration rate or interval measurements by trending information about a time associated with the particular class of respiration rate or interval measurements.

In Example 9, the method of one or any combination of Examples 1-8 optionally comprises integrating or otherwise lowpass filtering the collected respiration rate or interval measurements to obtain lowpass filtered collected respiration rate or interval measurements; detecting a change in the lowpass filtered collected respiration rate or interval measurements over a period of time; and providing the heart failure decompensation indication using the detected change in the lowpass filtered collected respiration rate or interval measurements.

In Example 10, the method of one or any combination of Examples 1-9 optionally comprises forming a histogram of the collected respiration rate or interval measurements; updating the histogram over time; detecting a change in the histogram over time; and providing the heart failure decompensation indication using the detected change in the histogram.

In Example 11, the method of one or any combination of Examples 1-10 optionally comprises classifying the respiration rate or interval measurements into nighttime respiration rate or interval measurements.

In Examples 12, the method of one or any combination of Examples 1-11 optionally comprises comparing daytime respiration rate or interval measurements to nighttime respirations rate or interval measurements.

In Example 13, the method of one or any combination of Examples 1-12 optionally comprises recording, in correspondence with the respiration rate or interval measurements, at least one of a corresponding posture, activity level, and angle of reclination.

In Example 14, the method of one or any combination of Examples 1-13 optionally comprises recording, in correspondence with the respiration rate or interval measurements, at least one of a heart rate, heart sound, heart rate variability, blood pressure, and impedance.

Example 15 includes an apparatus comprising means for detecting a respiration signal from a subject; means for determining respiration rate or interval measurements from the respiration signal; means for classifying the respiration rate or interval measurements into at least one class of respiration rate or interval measurements, the class corresponding to a specified time of day; means for trending information about the classified respiration rate or interval measurements of a particular class of respiration rate or interval measurements; and means for providing a heart failure decompensation indication using the trended information.

In Example 16, the apparatus of Example 15 optionally includes means for classifying the respiration rate or interval measurements into at least one of the following classes of respiration rate or interval measurements: a daily maximum respiration rate value, a daily minimum respiration rate value, a daily maximum respiration rate variability value, a daily minimum respiration rate variability value, and a daily central respiration rate value.

In Example 17, the apparatus of one or any combination of Examples 15-16 optionally includes means for classifying the respiration rate or interval measurements into at least one class of respiration rate or interval measurements by classifying the respiration rate or interval measurements as a specified one of daytime or nighttime respiration rate or interval measurements.

In Example 18, the apparatus of one or any combination of Examples 15-17 optionally includes means for collecting the specified one of the daytime or nighttime respiration rate or interval measurements; means for performing a statistical analysis on the collected respiration rate or interval measurements; and means for providing the heart failure decompensation indication using a result of the statistical analysis.

In Example 19, the apparatus of one or any combination of Examples 15-18 optionally includes means for providing the heart failure decompensation indication by detecting a change over time in a measure of centrality of the collected respiration rate or interval measurements.

In Example 20, the apparatus of one or any combination of Examples 15-19 optionally includes means for providing the heart failure decompensation indication by detecting a change over time in a measure of spread or variance of the collected respiration rate or interval measurements.

In Example 21, the apparatus of one or any combination of Examples 15-20 optionally includes means for trending information about the classified respiration rate or interval measurements by trending information about a time associated with the particular class of respiration rate or interval measurements.

Example 22 includes an apparatus comprising a respiration sensor, configured to detect a respiration signal from a subject; a respiration rate or interval measurement detector circuit, coupled to the respiration sensor, the respiration rate or interval measurement detector circuit configured to determine respiration rate or interval measurements from the respiration signal; a processor circuit, comprising: a respiration rate or interval measurement classifier circuit, configured to classify the respiration rate or interval measurements into at least one class of respiration rate or interval measurements corresponding to a specified time of day; a trending circuit, configured to trend information about the classified respiration rate or interval measurements; and an indicator circuit, configured to provide a heart failure decompensation indication using the trended information.

In Example 23, the apparatus of Example 22 optionally includes classifying, within the respiration rate or interval measurement classifier unit, respiration rate or interval measurements into at least one of the following respiration rate or interval measurement classes: a daily maximum respiration rate value, a daily minimum respiration rate value, a daily maximum respiration rate variability value, a daily minimum respiration rate variability value, and a daily central respiration rate value.

In Example 24, the apparatus of one or any combination of Examples 22-23 optionally includes clock circuit, within the respiration rate or interval measurement classifier circuit, which is configured to classify the respiration rate or interval measurements according to the time of day.

In Example 25, the apparatus of one or any combination of Examples 22-24 optionally includes a data centrality measurement circuit, configured to compute a measure of centrality of the specified one of the daytime respiration rate or interval measurements or nighttime respiration rate or interval measurements, and wherein the trending circuit is configured to trend the measure of centrality of the specified one of the nighttime or daytime respiration rate or interval measurements over a period of time; a data comparator circuit, coupled to the data centrality measurement circuit, the data comparator circuit configured to detect a change in the measure of centrality of the specified one of the nighttime or daytime respiration rate or interval measurements over the period of time; and wherein the indicator circuit is configured to provide the heart failure decompensation indication using the change in the measure of centrality of the specified one of the nighttime or daytime respiration rate or interval measurements over the period of time.

In Example 26, the apparatus of one or any combination of Examples 22-25 optionally includes a data aggregation circuit, configured to aggregate the specified one of the nighttime or daytime respiration rate or interval measurements; a statistical analysis circuit, coupled to the data aggregation circuit, the statistical analysis circuit configured to perform a statistical analysis on the aggregated specified one of the nighttime or daytime respiration rate or interval measurements; and wherein the indicator circuit is configured to provide the heart failure decompensation indication using a result of the statistical analysis.

In Example 27, the apparatus of one or any combination of Examples 22-26 optionally includes the indicator circuit configured to provide the heart failure decompensation indication by detecting a change over time in a measure of centrality of the specified one of the nighttime or daytime respiration rate or interval measurements.

In Example 28, the apparatus of one or any combination of Examples 22-27 optionally includes the indicator circuit configured to provide the heart failure decompensation indication by detecting a change over time in a measure of spread or variance of the specified one of the nighttime or daytime respiration rate or interval measurements.

In Example 29, the apparatus of one or any combination of Examples 22-28 optionally includes the trending circuit configured to trend information about a time associated with the particular class of respiration rate or interval measurements.

In Example 30, the apparatus of one or any combination of Examples 22-29 optionally includes an integrator or lowpass filter, configured to integrate or otherwise lowpass filter the specified one of the nighttime or daytime respiration rate or interval measurements to obtain lowpass filtered respiration rate or interval measurements; a data comparator circuit, coupled to the integrator or lowpass filter, the data comparator circuit configured to detect a change in the one of the lowpass filtered respiration rate or interval measurements over a period of time; and wherein the indicator circuit is configured to provide the heart failure decompensation indication using the detected change in the lowpass filtered respiration rate or interval measurements.

In Example 31, the apparatus of one or any combination of Examples 22-30 optionally includes a histogram memory, configured to store a histogram of the specified one of the nighttime or daytime respiration rate or interval measurements, wherein the histogram is configured to be updated over time; a histogram memory, configured to store a histogram of the successive differences in the specified one of the nighttime or daytime respiration rate or interval measurements, wherein the histogram is configured to be updated over time; a data comparator circuit, coupled to the histogram memories, the data comparator circuit configured to detect a change in the histogram over time; and wherein the indicator circuit is configured to provide the heart failure decompensation indication using the detected change in the histograms.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

The patent or application file contains at least one drawing executed in color. Copies of this patent or patent application publication with color drawing(s) will be provided by the Office upon request and payment of the necessary fee.

DETAILED DESCRIPTION

Figure 1:
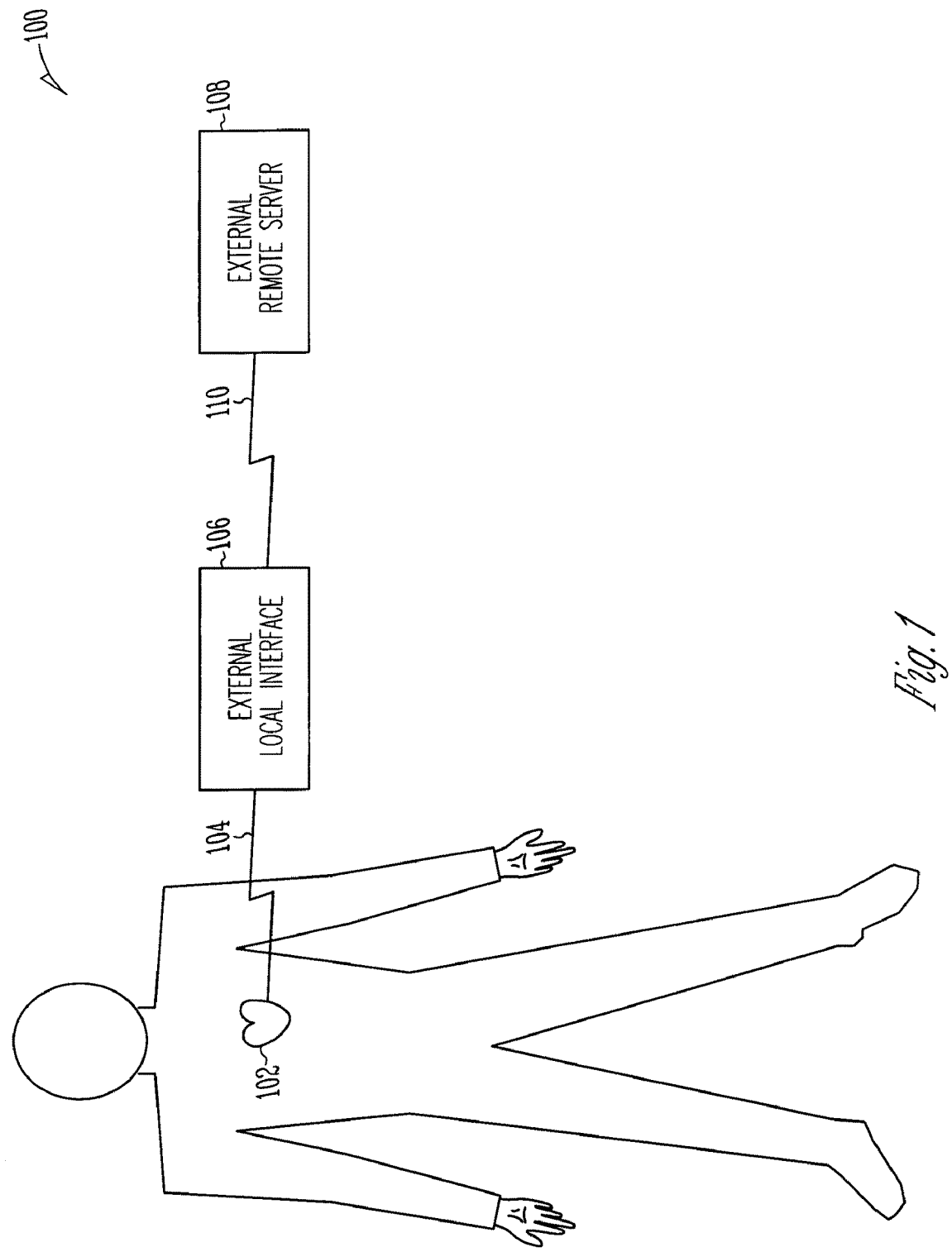
FIG. 1 is a block diagram illustrating generally an example of a system for monitoring respiration rate measurements.

FIG. 1 is a block diagram illustrating generally an example of a system 100 including a device 102, which is typically wirelessly communicatively coupled by a communication link 104 to an external local interface 106. In certain examples, the external local interface 106 is, in turn, generally communicatively coupled to an external remote server 108, such as over a wired or wireless telecommunications or computer network 110. Device 102 includes (by way of example, but not by way of limitation) a respiration sensor, a pacer, a defibrillator, a cardiac resynchronization therapy (CRT) device, a neurostimulation device, a device that combines more than one of these functions, or any other implantable or external device for diagnosing or treating one or more medical conditions. Device 102 can be an implantable device (as illustrated), or it may be an external device.

Figure 2:
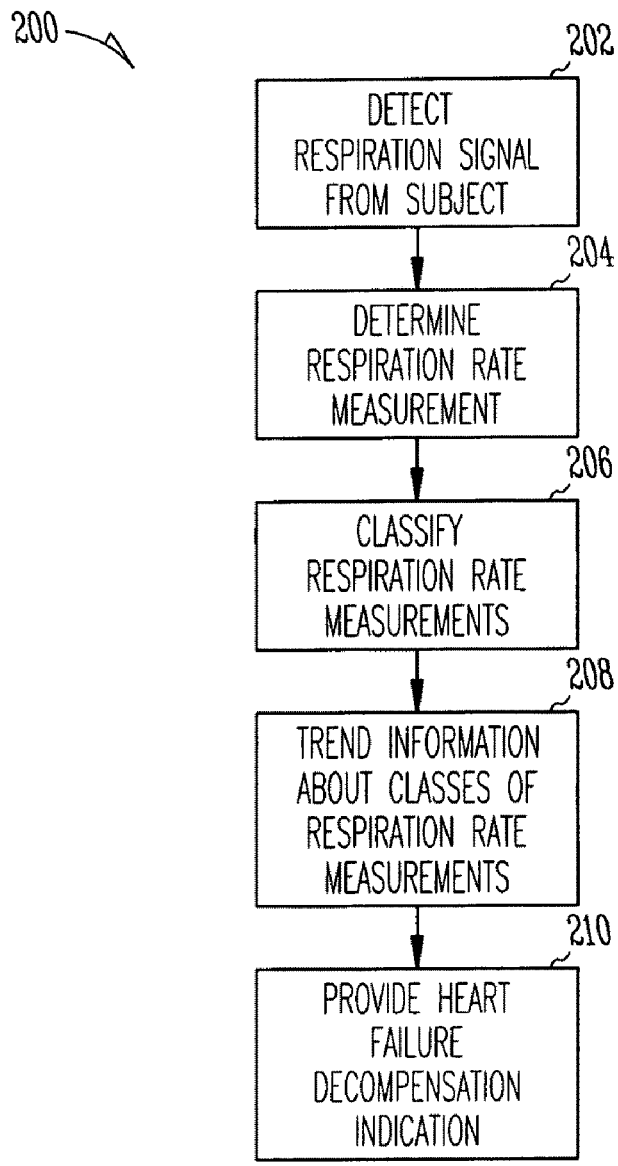
FIG. 2 is a flow chart illustrating an overview of a method for assessing heart failure decompensation based on respiration rate measurements.

FIG. 2 is a flow chart illustrating an overview of a method 200 for assessing heart failure decompensation based on respiration rate, such as by using the system 100. At 202, a respiration signal is detected from the subject. The respiration signal may be generated, for example, using one or more implantable or external sensors, such as an implantable transthoracic impedance sensor, an external respiratory band having piezoelectric or another sensor element, a respiratory mask airflow sensor, an accelerometer, or one or more other types of respiration sensors. At 204, a respiration rate measurement is determined using the respiration signal. Respiration rate variability can be computed from the respiration rate measurements. In determining the respiration rate measurements from the respiration signal, one or more periods of apneic breathing can be excluded. In addition, at least one of a corresponding posture, physical activity level, and angle of reclination can be recorded in correspondence with the respiration rate measurements, such as to determine whether the patient is in a consistent state with respect to one or more of these variables at the time of the respiration rate measurements. Further, at least one of a heart rate, heart sound, heart rate variability, blood pressure, and impedance can be recorded in correspondence with the respiration rate measurements, such as to assess one or more of these variables at one or more respiration rates. At 206, the respiration rate measurements are classified into at least one class of respiration rate measurements. In certain examples, the class corresponds to a specified time of day. At 208, information about one or more particular classes of respiration rate measurements is trended over time. Trending information about a particular class of respiration measurements can include trending information about a time associated with the particular class of respiration rate measurements, wherein the time is a specific time of day or night. At 210, a heart failure decompensation indication is provided, such as based on the trended information about one or more classes of respiration rate measurements.

Figure 3:
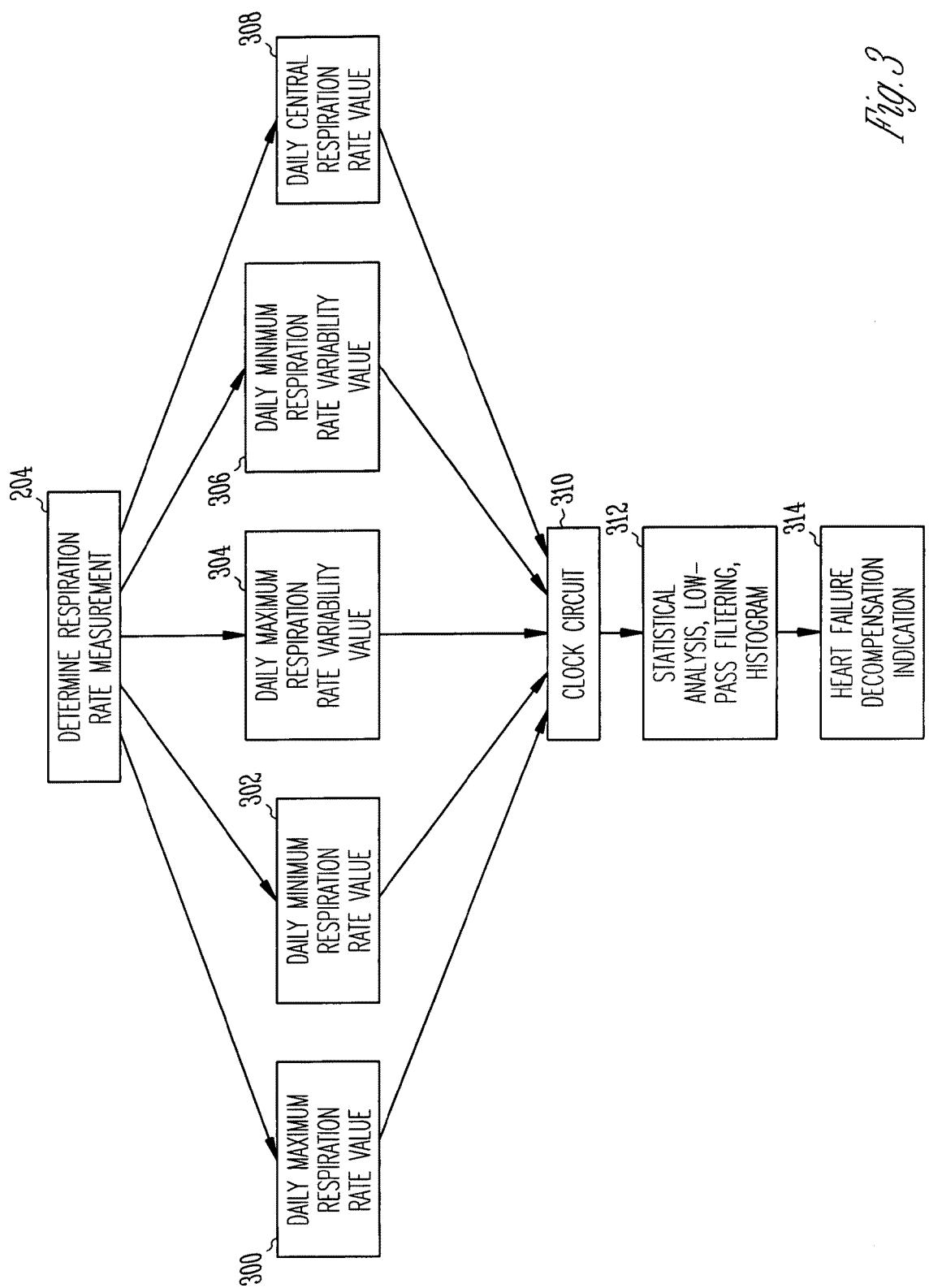
FIGS. 3 and 4 are flow charts illustrating different examples of parts of a method for assessing heart failure decompensation based on respiration rate measurements.
Figure 4:
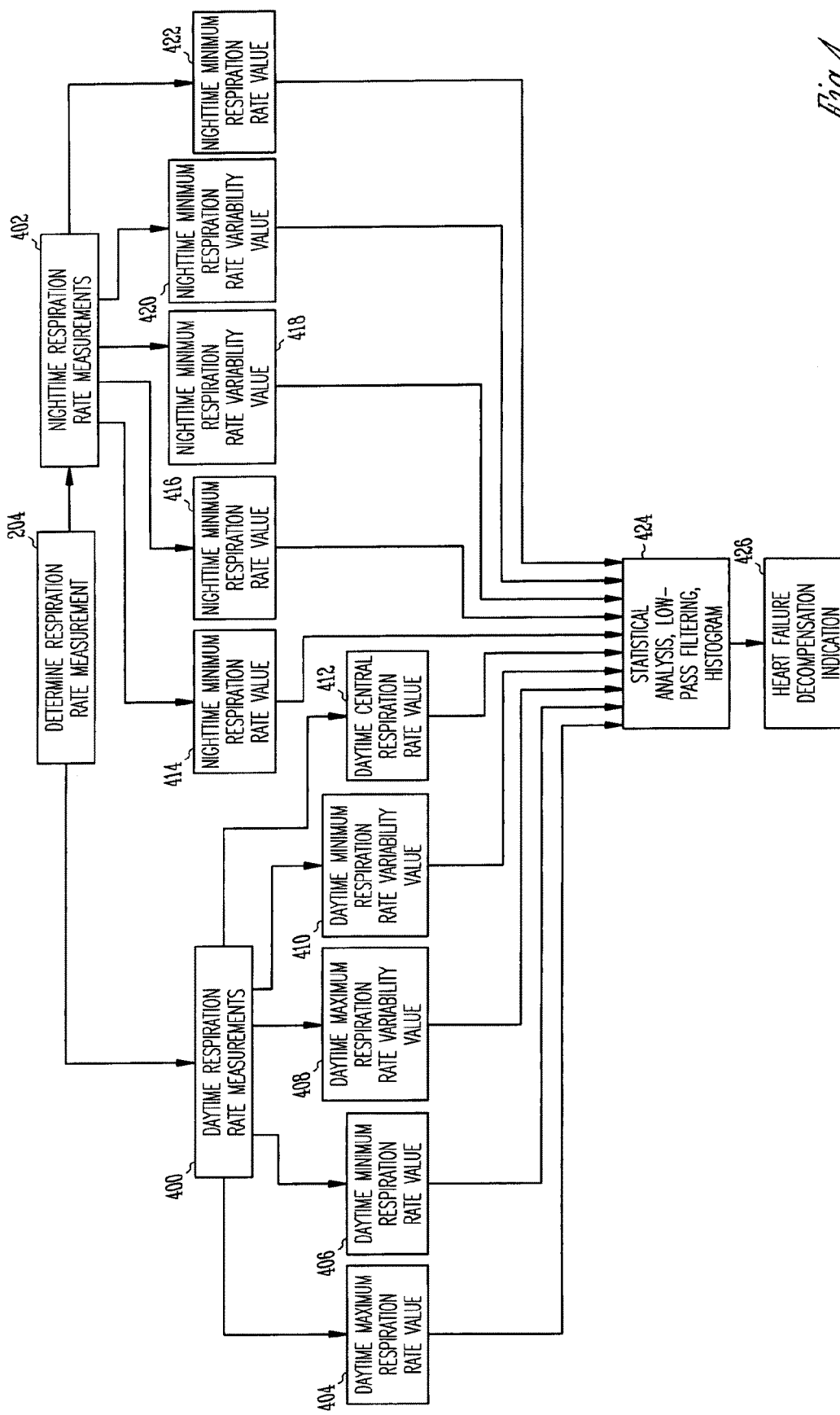

FIG. 3 and FIG. 4 illustrate two different examples of parts of the method described above with respect to FIG. 2. In FIG. 3, respiration rate measurements are first classified into at least one class of respiration rate measurements, and then the classified respiration rate measurements are associated with the corresponding time of day. In FIG. 4, the respiration rate measurements are first associated with the corresponding time of day and then classified into at least one class of respiration rate measurements. In FIG. 3 at 204, a respiration rate measurement is determined using the respiration signal, such as described above. At 300-308, the respiration rate measurement is classified into at least one of the following classes: a daily maximum respiration rate value 300, a daily minimum respiration rate value 302, a daily maximum respiration rate variability value 304, a daily minimum respiration rate variability value 306, or a daily central respiration rate value 308. At 310, the clock circuit further classifies the classified respiration rate measurements based on the corresponding time of day.

At 312, trended information is obtained using at least one class of respiration rate measurements. The trended information can be used to compute, for example, a statistical analysis of the specified class of respiration rate measurements. The statistical analysis can be used for detecting a change over time in a measure of centrality of the collected respiration rate measurements or detecting a change over time in a measure of spread or variance of the collected respiration rate measurements. In another example, the trended information can involve integrating or otherwise low-pass filtering the specified class of respiration rate measurements. In certain examples, the trended information can involve forming a histogram of the specified class of respiration rate measurements, updating the histogram over time, and detecting a change in the histogram over time. In general, changes in the time span associated with a classified respiration rate measurement may be indicative of heart failure decompensation.

At 314, a heart failure decompensation indication is determined and provided using the trended information described at 312. The heart failure decompensation indication can be included within an implantable device, such as 102, or an external device, such as 106 or 108. The heart failure decompensation indication can be used to provide an alert that is triggered, for example, by comparing the heart failure decompensation indication to a specified threshold value, or by a specified percent change from baseline of the heart failure decompensation indication. In certain examples, the alert or the heart failure decompensation indication may be provided in the form of an audio or visual signal on the local external device 106 or an electronic message sent to the remote external device 108.

In FIG. 4 at 204, a respiration rate measurement is determined using the respiration signal, such as described above with respect to FIG. 2. At 400 and 402, the respiration rate measurements are classified into daytime respiration rate measurements 400, or nighttime respiration rate measurements 402. Nighttime respiration rate measurements, when trended over time and compared to daytime respiration rate measurements, are particularly valuable in evaluating heart failure decompensation. Nighttime respiration rate measurements are taken during the "core sleep hours," during which respiration is less likely to be affected by talking, physical activity, posture, or conscious patient control of breathing. In certain examples, the daytime period is determined using a clock to select times from 5 am to midnight (05:00:00 to 23:59:59) as daytime, and to select times from midnight to 5 am (00:00:00 to 04:45:49) as nighttime.

At 404-422, the daytime and nighttime respiration rate measurements are further classified into at least one of the following classes: daytime or nighttime maximum respiration rate value 404 or 414, daytime or nighttime minimum respiration rate value 406 or 416, daytime or nighttime maximum respiration rate variability value 408 or 418, daytime or nighttime minimum respiration rate variability value 410 or 420, and daytime or nighttime central respiration rate value 412 or 422. At 424, trended information is obtained using at least one class of a specified daytime or nighttime respiration rate measurement. The trended information can be used to compute, for example, a statistical analysis of the specified class of respiration rate measurements. The statistical analysis can be used for detecting a change over time in a measure of centrality of the collected respiration rate measurements or detecting a change over time in a measure of spread or variance of the collected respiration rate measurements. In another example, the trended information can involve integrating or otherwise low-pass filtering the specified class of respiration rate measurements. In certain examples, the trended information can involve forming a histogram of the specified class of respiration rate measurements, updating the histogram over time, and detecting a change in the histogram over time. At 426, a heart failure decompensation indication is determined and provided using the trended information described at 424. The heart failure decompensation indication can be included within an implantable device, such as 102, or an external device, such as 106 or 108. The heart failure decompensation indication can be used to provide an alert that is triggered, for example, by comparing the heart failure decompensation indication to a specified threshold value, or by a specified percent change from baseline of the heart failure decompensation indication. In certain examples, the alert or the heart failure decompensation indication may be provided in the form of an audio or visual signal on the local external device 106 or an electronic message sent to the remote external device 108.

Figure 5:
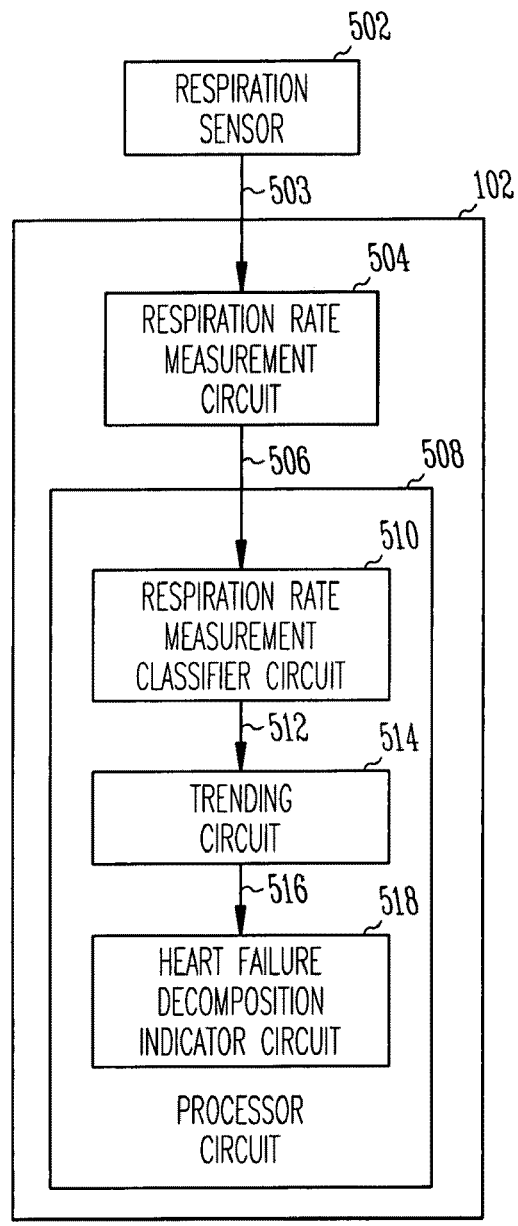
FIG. 5 is a block diagram generally illustrating an example of the structures and processes taking place within a device used to monitor respiration rate measurements.

FIG. 5 is a block diagram generally illustrating an example of the structures and processes taking place in association with the implantable or external device 102. A respiration sensor 502 may be external to device 102, as illustrated, or the respiration sensor 502 may be included within device 102. The respiration signal detected by the respiration sensor 502 is communicated at 503 to the respiration rate measurement circuit 504. The respiration rate measurement produced by the respiration rate measurement circuit 504 is communicated at 506 to the respiration rate measurement classifier circuit 510. The respiration rate measurement classifier circuit 510 classifies a respiration measurement into at least one of the following classes: a daily maximum respiration rate value, a daily minimum respiration rate value, a daily maximum respiration rate variability value, a daily minimum respiration rate variability value, or a daily central respiration rate value. The classified respiration rate measurements produced by the respiration rate measurement classifier circuit 510 are then communicated at 512 to the trending circuit 514, where trended information about one or more particular classes of respiration rate measurements is produced. Trending information about a particular class of respiration measurements can include trending information about a time associated with the particular class of respiration rate measurements, wherein the time is a specific time of day or night. This trended information is then communicated at 516 to the heart failure decompensation indicator circuit 518, where a heart failure decompensation indication signal is produced using the trended information about one or more particular classes of respiration rate measurements. The respiration rate measurement classifier circuit 510, the trending circuit 514, and the heart failure decompensation indicator circuit 518 are included within the processor circuit 508, which is detailed further in FIG. 6 below. Components 504, 510, 514, and 518 may be included within the device 102, as shown. Alternatively, at least one of components 504, 510, 514, and 518 may be external to the device 102, such as within the local external interface 106 or the remote external interface 108.

Figure 6:
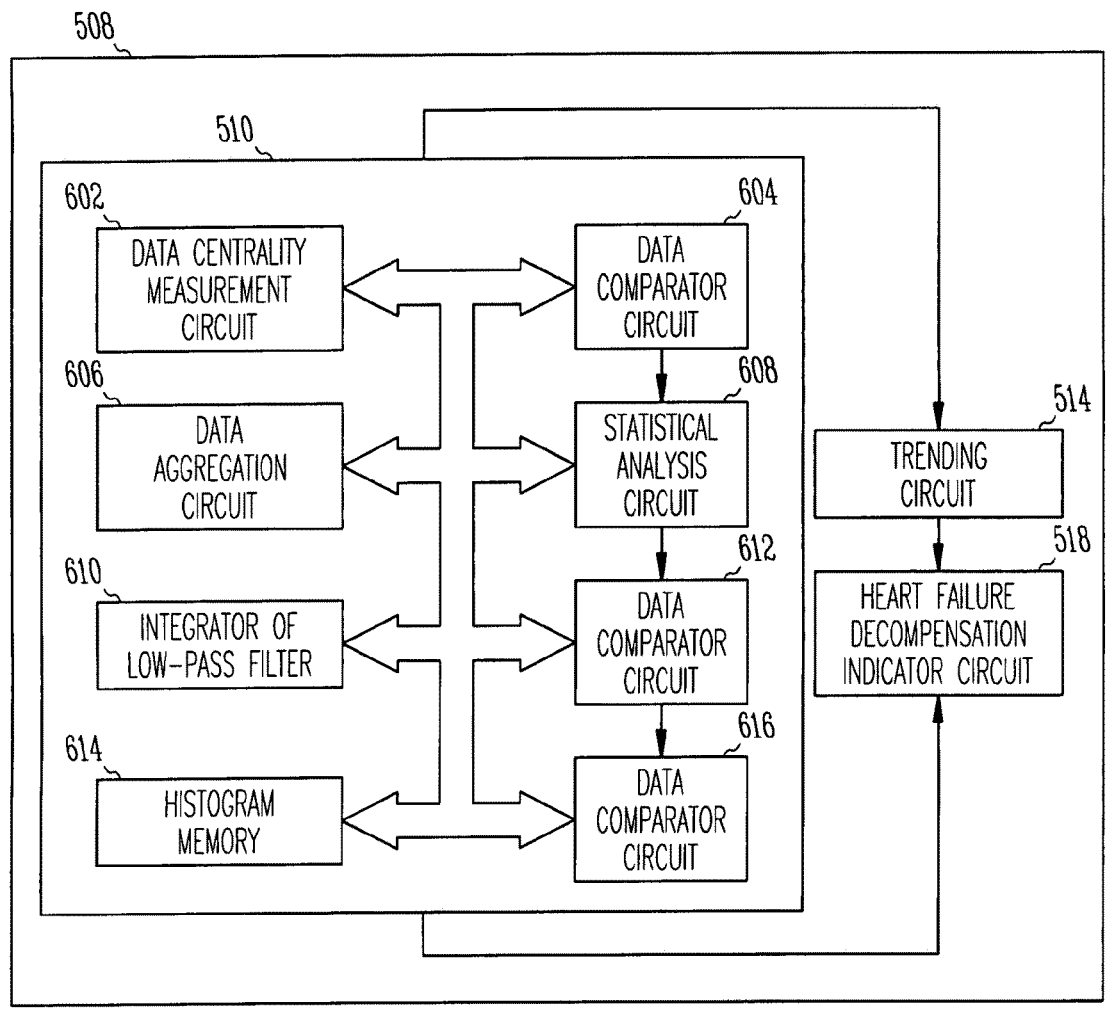
FIG. 6 is a block diagram further illustrating an example of portions of a device used to monitor respiration rate measurements.

FIG. 6 is a block diagram further illustrating an example of portions of the processor circuit 508. In this example, the respiration rate measurement classifier circuit 510 is included within the processor circuit 508. The components of the respiration rate measurement classifier circuit 510, such as those described below, communicate internally with one another. Information produced within the respiration rate measurement classifier circuit 510 is communicated to and displayed within the trending circuit 514. The information displayed within the trending circuit 514 is external to device 102. Information produced within the respiration rate measurement classifier circuit 510 and the trending circuit 514 is communicated to the heart failure decompensation indicator circuit 518. Both the trending circuit 514 and the heart failure decompensation indicator circuit 518 are included within the processor circuit 508, in this example.

In this example, the respiration rate measurement classifier unit 510 includes the data centrality measurement circuit 602 and the data comparator circuit 604. The data centrality measurement circuit 602 is configured to compute a measurement of centrality of a specified one of nighttime respiration rate measurements or daytime respiration rate measurements, such as a mean or median nighttime respiration rate, or a mean or median daytime respiration rate. The data comparator circuit 604, which is coupled to the data centrality measurement circuit 602, detects a change in the measure of centrality of the specified one of nighttime or daytime respiration rate measurements over a period of time. The information generated by the data comparator circuit 604 is communicated to the heart failure decompensation indicator circuit 518, which is configured to produce a heart failure decompensation indication using the communicated information. In general, a shift in the measure of centrality of a class of respiration rate measurements can indicate worsening heart failure status, which can cause an increase in the heart failure indication. For example, an increase in the daily minimum respiration rate value over time may be a sign that the patient's heart failure statues is worsening. In another example, a shift in the time at which the daily minimum respiration rate value occurs, such as getting progressively earlier by moving from nighttime to daytime, can indicate worsening heart failure.

The respiration rate measurement classifier unit 510 can also include a data aggregation circuit 606 and a statistical analysis circuit 608. The data aggregation circuit 606 is configured to aggregate a specified one of the nighttime or daytime respiration rate measurements. The statistical analysis circuit 608, which is coupled to the data aggregation circuit 606, is configured to perform a statistical analysis on the aggregated specified one of daytime or nighttime respiration rate measurements. The information generated by the statistical analysis circuit 608 can include at least one of a detected change over time in the measure of centrality of the specified one of daytime or nighttime respiration rate measurements and a detected change over time in a measure of spread or variance of the specified one of daytime or nighttime respiration rate measurements. The information generated by the statistical analysis circuit 608 is then communicated to the heart failure decompensation indicator circuit 518, which is configured to produce a heart failure decompensation indication using the communicated information. Generally, a large spread in a specified daytime or nighttime respiration rate measurement can lead to worsening heart failure status and an increase in the heart failure decompensation indication. A consistent shift away from the baseline for a given respiration rate measurement can be a sign of worsening heart failure status.

In certain examples, the respiration rate measurement classifier circuit 510 includes an integrator or low-pass filter 610 and a data comparator circuit 612. The integrator or low-pass filter 610 is configured to integrate or otherwise low-pass filter a specified one of daytime or nighttime respiration rate measurements. The data comparator circuit 612, which is coupled to the integrator or low-pass filter 610, is configured to detect a change in the specified one of daytime or nighttime low-pass filtered or integrated respiration rate measurements over a period of time. The information generated by the data comparator circuit 612 is communicated to the heart failure decompensation indicator circuit 518, which is configured to produce a heart failure decompensation indication using the communicated information. In general, a consistent shift over time or large range of low-pass filtered or integrated classified respiration rate measurements can be an indication of worsening heart failure status.

In certain examples, the respiration rate measurement classifier circuit 510 can include a histogram memory 614 and the data comparator circuit 616. The histogram memory 614 is configured to store a histogram of a specified one of daytime or nighttime respiration rate measurements. The histogram is configured to be updated over time. The data comparator circuit 616, which is coupled to the histogram memory 614, is configured to detect a change in the histogram over time. The information generated by the data comparator circuit 616 is communicated to the heart failure decompensation indicator circuit 518, which is configured to produce a heart failure decompensation indication using the communicated information. In general, a consistent shift over time or a large degree of variability in the trended histogram data can be a sign of worsening heart failure status.

Figure 7:
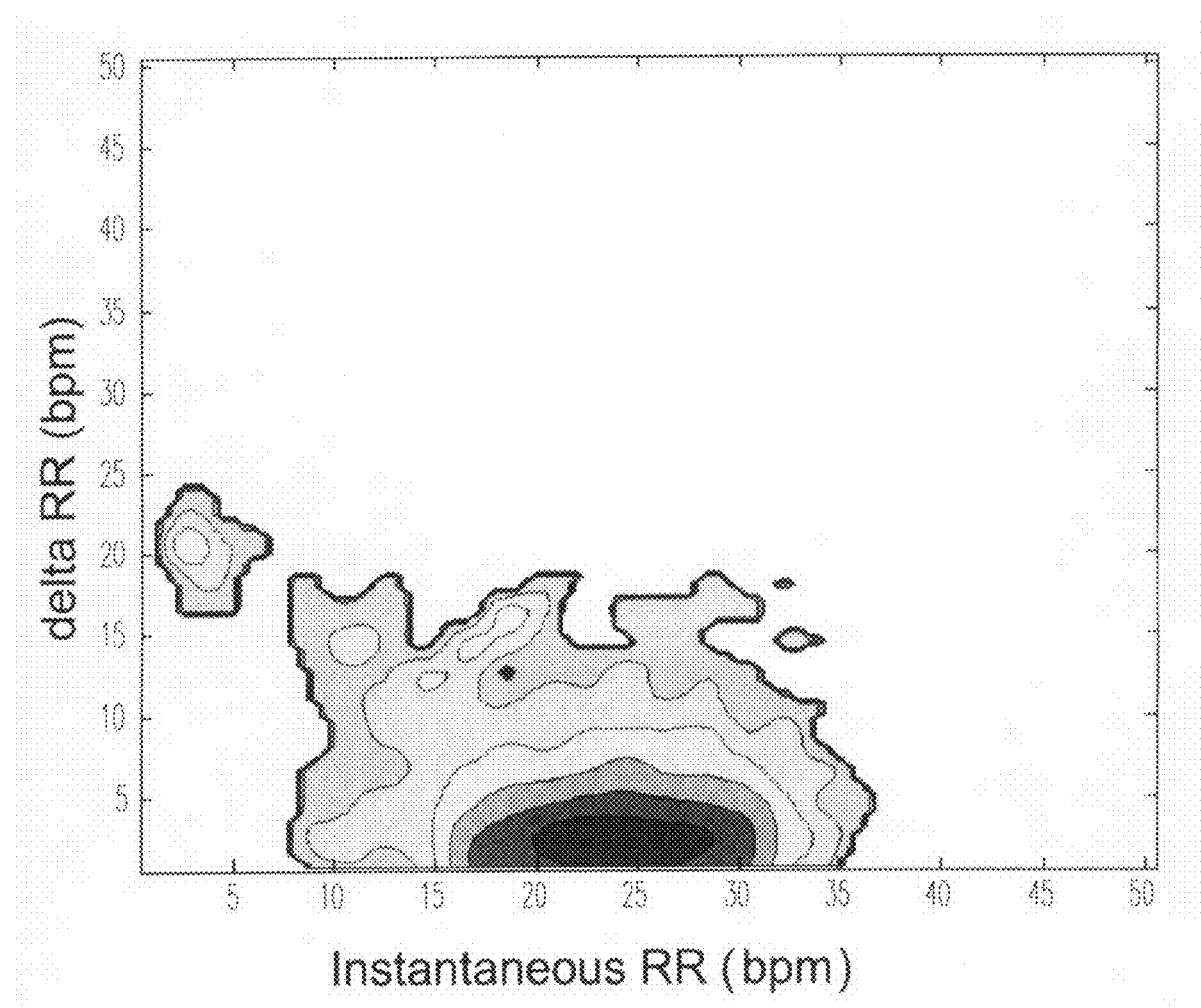
FIG. 7 is a diagram of an example of a statistical analysis performed on specified class of respiration rate measurements.

FIG. 7 is a diagram of a nighttime respiration rate variability footprint, which is one example of a statistical analysis performed on a specified class of respiration rate measurements. In this example, the successive differences, or delta, in nighttime respiration rate (measured in breaths per minute) is plotted against the instantaneous nighttime respiration rate (measured in breaths per minute). Different colors indicate the rate of occurrence of each incident, with red representing the highest rate of occurrence and blue representing the lowest rate of occurrence. The diagram can be used to evaluate or detect changes in a subject's heart failure decompensation status.

Some Notes

In this document, certain examples have been described with respect to using a "respiration rate measurement," for illustrative clarity. However, such examples can also be performed using a "respiration interval measurement" rather than a "respiration rate measurement," without departing from the scope of the described systems and methods.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   means for detecting a respiration signal from a subject;
   means for determining respiration rate or interval measurements from the respiration signal;
   means for classifying the respiration rate or interval measurements into at least one class of respiration rate or interval measurements and for associating a specified time of day with the at least one class;
   means for trending at least one of: (1) time of occurrence information about the classified respiration rate or interval measurements of a particular class of respiration rate or interval measurements, or (2) respiration rate or interval measurement information repeatedly, over a period of multiple days, during a specified one of a daytime subperiod or a nighttime subperiod, wherein the specified one of the daytime subperiod or the nighttime subperiod corresponds to the same specified time of day during each of the multiple days; and
   means for providing a heart failure decompensation indication using the trended information.

2. The apparatus of claim 1, wherein the means for classifying the respiration rate or interval measurements into at least one class of respiration rate or interval measurements includes the following classes: a daily maximum respiration rate value, a daily minimum respiration rate value, a daily maximum respiration rate variability value, a daily minimum respiration rate variability value, and a daily central respiration rate value.

3. The apparatus of claim 1, wherein the means for classifying the respiration rate or interval measurements into at least one class of respiration rate or interval measurements includes means for classifying the respiration rate or interval measurements as a specified one of daytime or nighttime respiration rate or interval measurements.

4. The apparatus of claim 3, comprising:
   means for collecting the specified one of the daytime or nighttime respiration rate or interval measurements;
   means for performing a statistical analysis on the collected respiration rate or interval measurements; and
   means for providing the heart failure decompensation indication using a result of the statistical analysis.

5. The apparatus of claim 4, comprising means for providing the heart failure decompensation indication by detecting a change over time in a measure of centrality of the collected respiration rate or interval measurements.

6. The apparatus of claim 4, comprising means for providing the heart failure decompensation indication by detecting a change over time in a measure of spread or variance of the collected respiration rate or interval measurements.

7. The method of claim 1, wherein the means for trending information about the classified respiration rate or interval measurements comprises trending information about a time associated with the particular class of respiration rate or interval measurements.

8. An apparatus comprising:
   a respiration sensor, configured to detect a respiration signal from a subject;
   a respiration rate or interval measurement detector circuit, coupled to the respiration sensor, the respiration rate or interval measurement detector circuit configured to determine respiration rate or interval measurements from the respiration signal;
   a processor circuit, comprising:
      a respiration rate or interval measurement classifier circuit, configured to classify the respiration rate or interval measurements into at least one class of respiration rate or interval measurements, and configured to associate a specified time of day with the at least one class;
      a trending circuit, configured to trend at least one of: (1) time of occurrence information about the classified respiration rate or interval measurements, or (2) respiration rate or interval measurement information repeatedly, over a period of multiple days, during a specified one of a daytime subperiod or a nighttime subperiod, wherein the specified one of the daytime subperiod or the nighttime subperiod corresponds to the same specified time of day during each of the multiple days; and
      an indicator circuit, configured to provide a heart failure decompensation indication using the trended information.

9. The apparatus of claim 8, wherein the respiration rate or interval measurement classifier unit classifies respiration rate or interval measurements into at least one of the following respiration rate or interval measurement classes: a daily maximum respiration rate value, a daily minimum respiration rate value, a daily maximum respiration rate variability value, a daily minimum respiration rate variability value, and a daily central respiration rate value.

10. The apparatus of claim 8, wherein the respiration rate or interval measurement classifier circuit includes a clock circuit that is configured to classify the respiration rate or interval measurements according to the time of day.

11. The apparatus of claim 10, comprising:
    a data centrality measurement circuit, configured to compute a measure of centrality of the specified one of the daytime respiration rate or interval measurements or nighttime respiration rate or interval measurements, and wherein the trending circuit is configured to trend the measure of centrality of the specified one of the nighttime or daytime respiration rate or interval measurements over a period of time;
    a data comparator circuit, coupled to the data centrality measurement circuit, the data comparator circuit configured to detect a change in the measure of centrality of the specified one of the nighttime or daytime respiration rate or interval measurements over the period of time; and
    wherein the indicator circuit is configured to provide the heart failure decompensation indication using the change in the measure of centrality of the specified one of the nighttime or daytime respiration rate or interval measurements over the period of time.

12. The apparatus of claim 10, comprising:
    a data aggregation circuit, configured to aggregate the specified one of the nighttime or daytime respiration rate or interval measurements;

a statistical analysis circuit, coupled to the data aggregation circuit, the statistical analysis circuit configured to perform a statistical analysis on the aggregated specified one of the nighttime or daytime respiration rate or interval measurements; and wherein the indicator circuit is configured to provide the heart failure decompensation indication using a result of the statistical analysis.

13. The apparatus of claim 12, wherein the indicator circuit is configured to provide the heart failure decompensation indication by detecting a change over time in a measure of centrality of the specified one of the nighttime or daytime respiration rate or interval measurements.

14. The apparatus of claim 12, wherein the indicator circuit is configured to provide the heart failure decompensation indication by detecting a change over time in a measure of spread or variance of the specified one of the nighttime or daytime respiration rate or interval measurements.

15. The apparatus of claim 8, wherein the trending circuit comprises trending information about a time associated with the particular class of respiration rate or interval measurements.

16. The apparatus of claim 10, comprising:

an integrator or lowpass filter, configured to integrate or otherwise lowpass filter the specified one of the nighttime or daytime respiration rate or interval measurements to obtain lowpass filtered respiration rate or interval measurements;

a data comparator circuit, coupled to the integrator or lowpass filter, the data comparator circuit configured to detect a change in the one of the lowpass filtered respiration rate or interval measurements over a period of time; and wherein the indicator circuit is configured to provide the heart failure decompensation indication using the detected change in the lowpass filtered respiration rate or interval measurements.

17. The apparatus of claim 10, comprising:

a histogram memory, configured to store a histogram of the specified one of the nighttime or daytime respiration rate or interval measurements, wherein the histogram is configured to be updated over time;

a histogram memory, configured to store a histogram of the successive differences in the specified one of the nighttime or daytime respiration rate or interval measurements, wherein the histogram is configured to be updated over time;

a data comparator circuit, coupled to the histogram memories, the data comparator circuit configured to detect a change in the histogram over time; and wherein the indicator circuit is configured to provide the heart failure decompensation indication using the detected change in the histograms.

\* \* \* \* \*